(12) United States Patent
Nihei et al.

(10) Patent No.: US 9,123,901 B2
(45) Date of Patent: Sep. 1, 2015

(54) PHOTOELECTRIC CONVERSION ELEMENT AND SOLID-STATE IMAGING DEVICE

(75) Inventors: Ayumi Nihei, Tokyo (JP); Masaki Murata, Tokyo (JP); Norihito Kobayashi, Kanagawa (JP)

(73) Assignee: Sony Corporation, Tokyo (JP)

( * ) Notice: Subject to any disclaimer, the term of this patent is extended or adjusted under 35 U.S.C. 154(b) by 175 days.

(21) Appl. No.: 13/807,403

(22) PCT Filed: Jun. 24, 2011

(86) PCT No.: PCT/JP2011/065133
§ 371 (c)(1),
(2), (4) Date: Dec. 28, 2012

(87) PCT Pub. No.: WO2012/005174
PCT Pub. Date: Jan. 12, 2012

(65) Prior Publication Data
US 2013/0099225 A1    Apr. 25, 2013

(30) Foreign Application Priority Data
Jul. 9, 2010  (JP) ................. 2010-156643

(51) Int. Cl.
*H01L 51/00* (2006.01)
*H01L 51/44* (2006.01)
*C07D 493/06* (2006.01)
(Continued)

(52) U.S. Cl.
CPC .......... *H01L 51/0073* (2013.01); *C07D 493/06* (2013.01); *H01L 27/14665* (2013.01); *H01L 51/44* (2013.01); *H01L 27/307* (2013.01); *H01L 51/0058* (2013.01); *H01L 51/0068* (2013.01); *H01L 51/0076* (2013.01); *H01L 51/42* (2013.01)

(58) Field of Classification Search
None
See application file for complete search history.

(56) References Cited

U.S. PATENT DOCUMENTS

2006/0278869 A1* 12/2006 Hioki et al. .................. 257/40
2009/0289248 A1   11/2009 Kobayashi et al.
(Continued)

FOREIGN PATENT DOCUMENTS

JP      2006-339424 A   12/2006
JP      2007-088033 A    4/2007
(Continued)

OTHER PUBLICATIONS

Li and Meng, Organic Light-Emitting Materials and Devices, Taylor & Francis (2007), p. 484.*
(Continued)

*Primary Examiner* — Ling Choi
*Assistant Examiner* — Catherine S Branch
(74) *Attorney, Agent, or Firm* — Wolf, Greenfield & Sacks, P.C.

(57) ABSTRACT

Provided is a photoelectric conversion element including a photoelectric conversion material layer that is constituted by an organic material having more excellent sensitivity and responsiveness than those of conventional ones.
The photoelectric conversion element of the present invention includes (a-1) a first electrode 21 and a second electrode 22 which are disposed apart from each other, and
(a-2) a photoelectric conversion material layer 30 that is disposed between the first electrode 21 and the second electrode 22,
wherein the photoelectric conversion material layer 30 is formed of a dioxaanthanthrene-based compound represented by the following structural formula (1).

18 Claims, 5 Drawing Sheets

(51) Int. Cl.
 *H01L 27/146* (2006.01)
 *H01L 27/30* (2006.01)
 *H01L 51/42* (2006.01)

(56) References Cited

U.S. PATENT DOCUMENTS

| | | |
|---|---|---|
| 2010/0013381 A1 | 1/2010 | Stoessel et al. |
| 2010/0032548 A1 | 2/2010 | Murata |
| 2013/0134409 A1 | 5/2013 | Nihei et al. |

FOREIGN PATENT DOCUMENTS

| | | |
|---|---|---|
| JP | 2007-123707 A | 5/2007 |
| JP | 2007-311647 A | 11/2007 |
| JP | 2009-029746 A | 2/2009 |
| JP | 2009-544743 A | 12/2009 |
| JP | 2010-006794 A | 1/2010 |

OTHER PUBLICATIONS

Kobayashi et al., Stable peri-xanthenoxanthene thin-film transistors with efficient carrier injection. Chem. Mater. 2009;21(3):552-6.

Higashino et al., Photovoltaic properties of azo compounds containing the thiazole group. J. Photochem. Photobiol. A: Chem. 1994;79:81-8.

Higashino et al., Yuki senryo azo kagobutsu no hikari dendo oyobi hikari kidenryoku ni okeru chikanki koka. Senryo to Yakuhin. 1996;41(6):135-49.

Kobayashi et al., kayosei peri-xanthenoxanthene yudotai o mochiita usumaku transistor. Dai 56 Kai Extended Abst. JP. Soci. Appl. Phys. Rel. Soc. Mar. 30, 2009;3;1390.

Possamai et al., Synthesis, photophysics and photoresponse of fullerene-based azoaromatic dyads. Chem. Eur. J. 2005;11:5765-76.

* cited by examiner

PHOTOELECTRIC CONVERSION ELEMENT AND SOLID-STATE IMAGING DEVICE

RELATED APPLICATIONS

This application is a U.S. National Stage application under 35 U.S.C. §371 based on International Application No. PCT/JP2011/065133, filed Jun. 24, 2011, which claims priority to Japanese Patent Application No. 2010-156643, filed Jul. 9, 2010, each of which is hereby incorporated by reference in its entirety for all purposes.

TECHNICAL FIELD

The present invention relates to a photoelectric conversion element and a solid-state imaging device comprising the photoelectric conversion element.

BACKGROUND ART

A photoelectric conversion element using an organic material (organic photodiode) can effect photoelectric conversion of only a specific color (wavelength zone). Furthermore, since the photoelectric conversion element has such characteristic, in the case when it is used as a photoelectric conversion element in a solid-state imaging device, it can provide a structure in which subpixels are laminated, which cannot be obtained by a conventional solid-state imaging device comprising subpixels each comprising a combination of an on-chip color filter (OCCF) and a photoelectric conversion element, wherein the subpixels are arranged in a two-dimensional fashion. Therefore, incident light can be received at a high efficiency, and thus it is expected that the sensitivity of the solid-state imaging device is enhanced. Furthermore, the photoelectric conversion element has an advantage that it does not require demosaicing, and thus a false color is not generated.

On the other hand, an organic photoelectric conversion element used in a solid-state imaging device has an identical or similar structure to that of various organic thin film solar cells (for example, see JP 2006-339424 A, JP 2007-123707 A, JP 2007-311647 A and JP 2007-088033 A) and aims at improving a photoelectric conversion rate.

CITATION LIST

Patent Documents

Patent Document 1: JP 2006-339424 A
Patent Document 2: JP 2007-123707 A
Patent Document 3: JP 2007-311647 A
Patent Document 4: JP 2007-088033 A
Patent Document 5: JP 2010-006794 A

SUMMARY OF THE INVENTION

Problems to be Solved by the Invention

However, in general, organic materials have higher resistance and very low mobility and carrier density as compared to those of silicon-based semiconductor materials. Therefore, organic materials have not shown characteristics that are comparable to those of conventional photoelectric conversion elements using inorganic materials such as silicon-based semiconductor materials, in sensitivity and responsiveness. Meanwhile, the applicant of the present application has filed a patent application relating to a dioxaanthanthrene-based compound and a semiconductor device using the dioxaanthanthrene-based compound (Japanese Patent Application No. 2008-136292. See JP 2010-006794 A.) However, this patent application does not mention at all about a photoelectric conversion element and a solid-state imaging device.

Therefore, the present invention aims at providing a photoelectric conversion element comprising a photoelectric conversion material layer that is constituted by an organic material having more excellent sensitivity and responsiveness than those of conventional ones, and a solid-state imaging device comprising the photoelectric conversion element.

Solution to Problems

The photoelectric conversion element of the first embodiment or second embodiment of the present invention for achieving the above-mentioned purpose comprises (a-1) a first electrode and a second electrode which are disposed apart from each other, and (a-2) a photoelectric conversion material layer that is disposed between the first electrode and the second electrode, wherein the photoelectric conversion material layer is formed of a dioxaanthanthrene-based compound represented by the structural formula (1) [the first embodiment of the present invention] or the structural formula (2) [the second embodiment of the present invention] mentioned below.

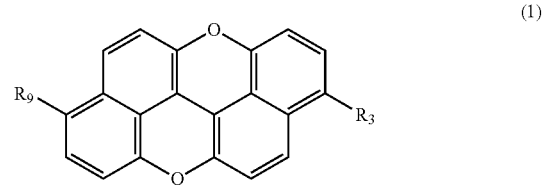

(1)

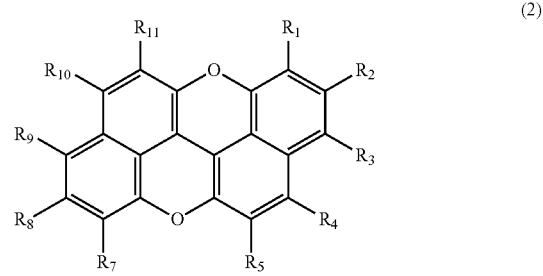

(2)

Provided that at least one of $R_3$ and $R_9$ is a substituent other than hydrogen in the structural formula (1), and at least one of $R_1$ to $R_{11}$ is a substituent other than hydrogen in the structural formula (2), and the substituent other than hydrogen is a substituent selected from the group consisting of an alkyl group, a cycloalkyl group, an alkenyl group, an alkynyl group, an aryl group, an arylalkyl group, an aromatic heterocycle, a heterocycle group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, an ureido group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group and a silyl group.

The solid-state imaging device of the first embodiment or second embodiment of the present invention for achieving the above-mentioned purpose comprises a photoelectric conversion element comprising (a-1) a first electrode and a second electrode which are disposed apart from each other, and (a-2) a photoelectric conversion material layer that is disposed between the first electrode and the second electrode, wherein the photoelectric conversion material layer is formed of the above-mentioned dioxaanthanthrene-based compound represented by the structural formula (1) [the first embodiment of the present invention] or the structural formula (2) [the second embodiment of the present invention].

Effects of the Invention

In the electric conversion element or solid-state imaging device according to the first embodiment or the second embodiment of the present invention, the dioxaanthanthrene-based compound that is suitable for constituting the photoelectric conversion material layer is packed into a π stack structure in a neutral state in which a voltage is not applied or an ionic state in which a voltage is applied. Therefore, the backbone of the dioxaanthanthrene-based compound may easily become a packing of a π stack structure in the photoelectric conversion material layer, without specifically introducing a bulky substituent. Therefore, the dioxaanthanthrene-based compound shows a high carrier mobility as 0.4 $cm^2/V \cdot s$ and thus is excellent in on-off response property of photocurrent by the presence or absence of light irradiation, and has a high degree of freedom in the molecular designing of an organic semiconductor material that constitutes the photoelectric conversion material layer, and therefore the molecular designing becomes easy. In addition, the process adaptivity can be improved. Namely, the photoelectric conversion material layer can be formed based on not only a PVD process but also so-called wet processes such as an application process and a printing process. Therefore, a photoelectric conversion element having high carrier mobility and high performance can be easily produced by this way. Furthermore, since substituents can be easily introduced and an absorption wavelength can be selected by selecting suitable substituents, it becomes possible to absorb light at a certain wavelength by the photoelectric conversion material layer. Therefore, in the case when a solid-state imaging device is constituted by the photoelectric conversion element of the present invention, an on-chip color filter is not necessary, and thus it becomes possible to constitute a photoelectric conversion element comprising multiple layers.

MODE FOR CARRYING OUT THE INVENTION

Figure 1:
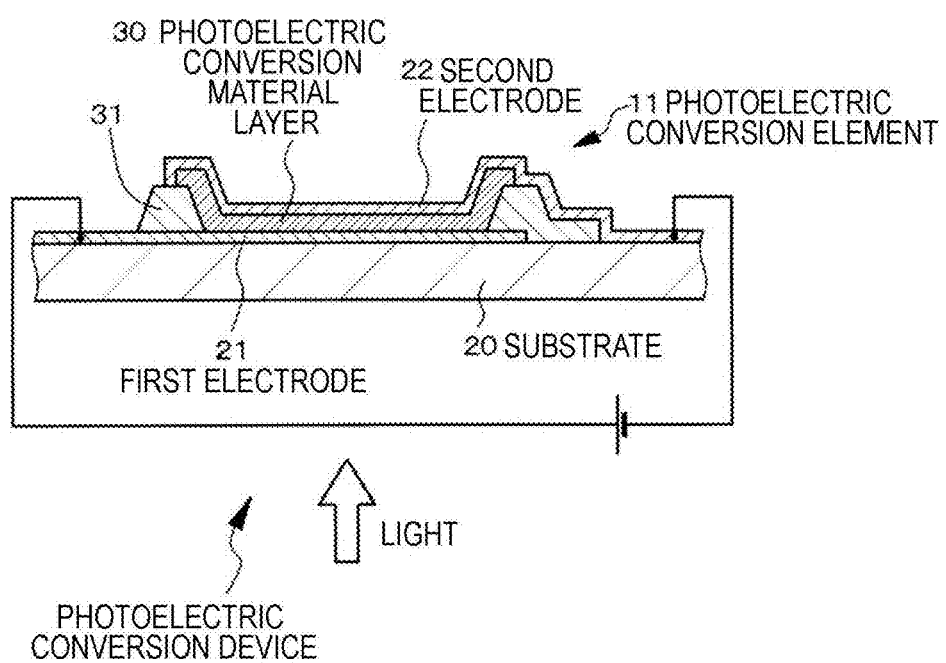
FIG. 1 is a schematic cross-sectional view of the photoelectric conversion element of Example 1.

Hereinafter the present invention will be explained based on Examples with referring to the drawings, but the present invention is not construed to be limited by Examples and the various numerical values and materials in Examples are for exemplification. The explanations will be made in the order shown below.

1. Generic explanations on the photoelectric conversion elements and solid-state imaging devices of the first embodiment and second embodiment of the present invention 2. Example 1 (The photoelectric conversion elements and solid-state imaging devices of the first embodiment and second embodiment of the present invention)

3. Example 2 (A modification of Example 1. A different dioxaanthanthrene-based compound was used.)

4. Example 3 (Another modification of Example 1. A different dioxaanthanthrene-based compound was used.)

5. Example 4 (Another modification of Example 1. A different dioxaanthanthrene-based compound was used.)

6. Example 5 (Another modification of Example 1. A different dioxaanthanthrene-based compound was used.)

7. Example 6 (Another modification of Example 1. A different dioxaanthanthrene-based compound was used.)

8. Example 7 (Another modification of Example 1. A different dioxaanthanthrene-based compound was used.)

9. Example 8 (Another modification of Example 1. A different dioxaanthanthrene-based compound was used.)

10. Example 9 (Another modification of Example 1. A different dioxaanthanthrene-based compound was used.)

11. Example 10 (Another modification of Example 1. A different dioxaanthanthrene-based compound was used.)

12. Example 11 (Another modification of Example 1. A different dioxaanthanthrene-based compound was used.)

13. Example 12 (Another modification of Example 1. A different dioxaanthanthrene-based compound was used.)

14. Example 13 (A modification of Example 1. Modification of structure of photoelectric conversion element.)

15. Example 14 (Another modification of Example 1. Modification of structure of photoelectric conversion element.), and others

[Generic Explanations on the Photoelectric Conversion Elements and Solid-State Imaging Devices of the First Embodiment and Second Embodiment of the Present Invention]

In the photoelectric conversion element, or the photoelectric conversion element in the solid-state imaging device according to the first embodiment or second embodiment of the present invention (hereinafter these will be collectively and simply referred to as "the photoelectric conversion element and the like of the present invention", a constitution in which a first electrode formed of a transparent electroconductive material is formed on a transparent substrate, a photoelectric conversion material layer is formed on the first electrode, and the second electrode is formed on the photoelectric conversion material layer can be formed. Alternatively, a constitution in which a first electrode is formed on a substrate, a photoelectric conversion material layer is formed on the first electrode, and a second electrode that is formed of a transparent electroconductive material is formed on the photoelectric conversion material layer can be formed. The first electrode and second electrode are disposed apart from each other, and as such parting state, an embodiment in which the second electrode is disposed above the first electrode can be exemplified.

In the photoelectric conversion element and the like of the present invention, as mentioned above, it is preferable that the electrode at the light-incidence side is formed of a transparent electroconductive material. Such electrode is referred to as a "transparent electrode". As a transparent electroconductive material that constitutes the transparent electrode, indium-tin oxides (including ITO, Sn-doped $In_2O_3$, crystalline ITO and amorphous ITO), IFO (F-doped $In_2O_3$), tin oxide ($SnO_2$), ATO (Sb-doped $SnO_2$), FTO (F-doped $SnO_2$), zinc oxide (including Al-doped ZnO and B-doped ZnO, and Ga-doped ZnO), indium oxide-zinc oxide (IZO), titanium oxide ($TiO_2$), spinel-type oxides, and an oxide having a $YbFe_2O_4$ structure can be exemplified. A transparent electrode formed of such material generally has a high work function and functions as an anode electrode. The method for forming the transparent electrode depends on the material that constitutes the transparent electrode, and physical vapor-phase deposition (PVD processes) such as a vacuum deposition process, a reactive deposition processes, a vacuum deposition process, a reactive deposition process, various sputtering processes, an electron beam deposition process and an ion plating process, and various chemical deposition processes (CVD processes) including a pyrosol process, a process by thermal decomposition of an organic metal compound, a spraying process, a dip process and an MOCVD process, an electroless plating process and an electroplating process can be exemplified. Where necessary, the other electrode may also be constituted by a transparent electroconductive material.

In the case when transparency is unnecessary, in the case when the first electrode or second electrode is functioned as an anode electrode (anode) as an electroconductive material that constitutes the first electrode or second electrode, i.e., functioned as an electrode from which holes are taken out, it is preferable to constitute the electrode by an electroconductive material having a high work function (for example, $\phi$=4.5 eV to 5.5 eV), and gold (Au), silver (Ag), chromium (Cr), nickel (Ni), palladium (Pd), platinum (Pt), iron (Fe), iridium (Ir), germanium (Ge), osmium (Os), rhenium (Re) and tellurium (Te) can be specifically exemplified. On the other hand, in the case when the first electrode or second electrode is functioned as a cathode electrode (cathode), i.e., functioned as an electrode from which electrons are taken out, it is preferable that the electrode is constituted by an electroconductive material having a low work function (for example, $\phi$=3.5 eV to 4.5 eV), and alkali metals (for example, Li, Na, K and the like) and fluorides or oxides thereof, alkali earth metals (for example, Mg, Ca and the like) and fluorides or oxides thereof, aluminum (Al), zinc (Zn), tin (Sn), thallium (Tl), sodium-potassium alloy, aluminum-lithium alloy, magnesium-silver alloy, rare earth metals such as indium and ytterbium, or alloys thereof can be specifically exemplified. Alternatively, as the material for constituting the first electrode or second electrode, electroconductive substances such as metals such as platinum (Pt), gold (Au), palladium (Pd), chromium (Cr), nickel (Ni), aluminum (Al), silver (Ag), tantalum (Ta), tungsten (W), copper (Cu), titanium (Ti), indium (In), tin (Sn), iron (Fe), cobalt (Co) and molybdenum (Mo), or alloys comprising these metal elements, electroconductive particles formed of these metals, electroconductive particles of alloys comprising these metals, polysilicons containing impurities, carbon-based materials, oxide semiconductors, carbon nanotubes and graphenes can be exemplified, and laminated structures of layers containing these elements can also be formed. In addition, as the materials for constituting the first electrode and second electrode, organic materials (electroconductive polymers) such as poly(3,4-ethylenedioxythiophene)/polystyrene sulfonic acid [PEDOT/PSS] can also be exemplified. Alternatively, these electroconductive materials may be mixed with a binder (polymer) to form a paste or ink, and the paste or ink may be cured and used as electrodes. The method for forming the first electrode and second electrode depends on the materials that constitute these electrodes, and examples may include combinations of any of various PVD processes; various CVD processes including an MOCVD process; various application processes; a lift-off process; a sol-gel process; an electrodeposition process; a shadow mask process; plating processes such as an electroplating process and an electroless plating process, or a combination thereof; and a spray process, with a patterning technique as necessary. As the substrate, organic polymers exemplified by polymethyl methacrylate (polymethyl methacrylate, PMMA) and polyvinyl alcohol (PVA), polyvinyl phenol (PVP), polyethersulfone (PES), polyimide, polycarbonate (PC), polyethylene telephthalate (PET) and polyethylene naphthalate (PEN) (these have forms of polymer materials such as plastic films, plastic sheets and plastic substrates having flexibility, which are constituted by polymer materials) can be exemplified, or mica can also be exemplified. If a substrate constituted by such flexible polymer material is used, for example, incorporation or integration into electronic devices becomes possible. Alternatively, as the substrate, various glass substrates, various glass substrates comprising insulating films formed on the surfaces, quartz substrates, quartz substrates comprising insulating films formed on the surfaces, silicon substrates comprising insulating films formed on the surfaces, and metal substrates formed of various alloys or various metals such as stainless can be exemplified. In addition, as the insulating films, silicon oxide-based materials (for example, $SiO_X$ and spin-on-glass (SOG)); silicon nitride ($SiN_Y$); silicon oxide nitride (SiON); aluminum oxide ($Al_2O_3$); metal oxides and metal salts can be exemplified. Alternatively, electroconductive substrates comprising these insulating films formed on the surfaces (substrates formed of metals such as gold and aluminum, and substrates formed of highly oriented graphite) can also be used. It is desirable that the surface of the substrate is smooth, but the surface may have roughness to the extent that the properties of the photoelectric conversion material layer are not adversely affected. The adhesion between the first electrode or second electrode and the substrate may be improved by forming a silanol derivative on the surface of the substrate by a silane coupling process, or by forming a thin film formed of a thiol derivative, a carboxylic acid derivative, a phosphoric acid derivative or the like by an SAM process or the like, or by forming a thin film formed of an insulating metal salt or metal complex by a CVD process or the like. The transparent substrate refers to a substrate constituted by a material that does not excessively absorb light that enters the photoelectric conversion material layer through the substrate.

Where necessary, the electrodes and photoelectric conversion material layer may be coated with coating layers. As the material for constituting the coating layers, not only inorganic-based insulating materials such as those exemplified by silicon oxide-based materials; silicon nitride ($SiN_Y$); and metal oxide highly dielectric insulating films such as aluminum oxide ($Al_2O_3$), but also organic-based insulating materials (organic polymers) such as those exemplified by polymethyl methacrylate (PMMA); polyvinyl phenol (PVP); polyvinyl alcohol (PVA); polyimide; polycarbonate (PC); polyethylene telephthalate (PET); polystyrene; silanol derivatives such as N-2(aminoethyl)-3-aminopropytrimethoxysilane (AEAPTMS), 3-mercaptopropytrimethoxysilane (MPTMS) and octadecyltrichlorosilane (OTS) (silane coupling agents); and linear hydrocarbons having a functional group that can bind to electrodes on one end such as octadecanethiol and dodecylisocyanate can be exemplified, or combinations of these can also be used. In addition, as the silicon oxide-based materials, silicon oxide ($SiO_x$), BPSG, PSG, BSG, AsSG, PbSG, silicon oxide nitride (SiON), SOG (spin-on-glass) and low dielectric materials (for example, polyaryl ethers, cycloperfluorocarbon polymers and benzocyclobutene, cyclic fluorine resins, polytetrafluoroethylene, fluoroaryl ethers, fluoropolyimides, amorphous carbon and organic SOG) can be exemplified.

Although the thickness of the photoelectric conversion material layer is not limited in the photoelectric conversion element and the like of the present invention, $2.5 \times 10^{-8}$ m to $3 \times 10^{-7}$ m, preferably $2.5 \times 10^{-8}$ m to $2 \times 10^{-7}$ m, and more preferably $1 \times 10^{-7}$ m to $1.8 \times 10^{-7}$ m can be exemplified. The dioxaanthanthrene-based compound represented by the structural formula (1) or structural formula (2) has a high carrier mobility (about 0.4 $cm^2/V \cdot sec$). Furthermore, it becomes possible to decrease the thickness of the photoelectric conversion material layer, and problems such as a high resistance, a low mobility and a low carrier density, which were the defects that conventional organic materials had, can be solved, and thereby a photoelectric conversion element or solid-state imaging device having high sensitivity and high-speed responsiveness can be provided. Meanwhile, electric field intensity E that is applied to the photoelectric conversion material layer when a same electric potential is applied can be increased by decreasing the thickness of the photoelectric conversion material layer, and thus it becomes possible to obtain a high photocurrent even the low mobility or carrier density is low.

As the method for forming the photoelectric conversion material layer, an application process, a PVD process; and various CVD processes including an MOCVD process can be exemplified. As the application process, a spin coat process; a dipping process; a casting process; various printing processes such as a screen printing process, an inkjet printing process, an offset printing process and a gravure printing process; a stamp process; a spray process; various coating processes such as an air doctor coater process; a blade coater process, a rod coater process, a knife coater process, a squeeze coater process, a reverse roll coater process, a transfer roll coater process, a gravure coater process, a kiss coater process, a cast coater process, a spray coater process, a slit orifice coater process and a calender coater can be specifically exemplified. As a solvent in the application process, nonpolar or low polar organic solvents such as toluene, chloroform, hexane and ethanol can be exemplified. As the PVD process, various vacuum deposition processes such as an electron beam heating process, a resistance heating process and a flash deposition process; a plasma deposition process; various sputtering processes such as a bipolar sputtering process, a direct current sputtering process, a direct current magnetron sputtering process, a high frequency wave sputtering process, a magnetron sputtering process, an ion beam sputtering process and a bias sputtering process; and various ion plating processes such as a DC (direct current) process, an RF process, a multicathode process, an activation reaction process, an electric field deposition process, a high frequency wave ion plating process and a reactive ion plating process can be exemplified. Alternatively, in the case when the photoelectric conversion element that constitutes the solid-state imaging device is integrated, a process for forming a pattern based on a PLD process (pulse laser deposition process) can be adopted.

The $R_a$ of a primer on which the photoelectric conversion material layer is to be formed, specifically, for example, the surface roughness $R_a$ of the first electrode and substrate is preferably 1.0 nm or less. By planarizing the primer, the molecules that constitute the photoelectric conversion material layer can be arranged in an orderly fashion on the plane primer in either the horizontal direction or vertical direction, thereby a structure in which significant potential descending is difficult to occur at the interface of the photoelectric conversion material layer and the first electrode is formed. Meanwhile, it is widely known that such potential descending is caused by lattice mismatch at the interface of the photoelectric conversion material layer and first electrode and leads to formation of a defect level and increase in interface resistance, and thereby inhibits carrier transfer between the first electrode and photoelectric conversion material layer. A planarization layer may be formed between the photoelectric conversion material layer and substrate. The planarization layer may have a function to prevent the reflection of light that has passed the substrate. The planarization layer can have a constitution formed of polymethyl methacrylate, polyvinyl alcohol, polyvinyl phenol, polyethersulfone, polyimide, polycarbonate, polyethylene telephthalate, polyethylene naphthalate, a silicon oxide-based material, silicon nitride, silicon oxide nitride or aluminum oxide.

The surface of the first electrode as a primer on which the photoelectric conversion material layer is to be formed may be subjected to a plasma ashing treatment. As a gas species for plasma ashing, at least one or more kind of gas species selected from Ar, $N_2$ and $O_2$ can be exemplified. By subjecting the surface of the first electrode to a plasma ashing treatment, unevenness and noise level in photoelectric conversion were decreased, and a dark current level could be decreased to 1 $nA/cm^2$ while retaining a photocurrent value. Furthermore, since a dark current level can be decreased as mentioned above, an organic photoelectric conversion element that has a wide dynamic range and can provide a contrast at high sensitivity can be consequently provided.

The dioxaanthanthrene-based compound represented by the structural formula (1) that constitutes the photoelectric conversion material layer in the photoelectric conversion element and the like of the first embodiment of the present invention is an organic semiconductor material in which at least one of the 3- and 9-positions in 6,12-dioxaanthanthrene (so-called peri-xanthenoxanthene, 6,12-dioxaanthanthrene, which is sometimes abbreviated as "PXX") is substituted with a substituent other than hydrogen. The dioxaanthanthrene-based compound represented by the structural formula (2) that constitutes the photoelectric conversion material layer in the photoelectric conversion element and the like of the second embodiment of the present invention is an organic semiconductor material in which at least one of the 1-, 2-, 3-, 4-, 5-, 7-, 8-, 9-, 10- and 11-positions of 6,12-dioxaanthanthrene is substituted with a substituent other than hydrogen.

Alternatively, the dioxaanthanthrene-based compound is obtained by halogenating peri-xanthenoxanthene to give 3,9-dihalo-peri-xanthenoxanthene, and substituting the halogen atom(s) with substituent(s), and is formed by substituting at least one of the 3- and 9-positions of 6,12-dioxaanthanthrene with the substituent(s) other than hydrogen. This case can be an embodiment wherein the halogen atoms are bromine (Br). Furthermore, in the dioxaanthanthrene-based compound comprising such embodiment, the substituents can be each an embodiment formed of an aryl group or an arylalkyl group, or the substituents can be each an embodiment formed of an aryl group in which at least one of the 2- to 6-positions is substituted with an alkyl group or an embodiment formed of an aryl group in which at least one of the 2- to 6-positions is substituted with an aryl group, or the substituents can be each an embodiment formed of a p-tolyl group, a p-ethylphenyl group, a p-isopropylphenyl group, a 4-propylphenyl group, a 4-butylphenyl group, a 4-nonylphenyl group or a p-biphenyl.

The photoelectric conversion element and the like according to the first embodiment of the present invention includes (1-1) the case wherein $R_3$ is a substituent other than hydrogen, and $R_9$ is a hydrogen atom, (1-2) the case wherein $R_9$ is a substituent other than hydrogen, and $R_3$ is a hydrogen atom, and (1-3) the case when $R_3$ and $R_9$ are each a substituent other than hydrogen. In the case (1-3), $R_3$ and $R_9$ may be the same substituent or different substituents.

On the other hand, in the photoelectric conversion element and the like according to the second embodiment of the present invention, (2-1) the cases wherein $R_1$ is a substituent other than hydrogen and $R_2$ to $R_{11}$ are each a substituent other than hydrogen or a hydrogen atom (29 cases in total), (2-2) the cases wherein $R_2$ is a substituent other than hydrogen and $R_1$ and $R_3$ to $R_{11}$ are each a substituent other than hydrogen or a hydrogen atom (29 cases in total), (2-3) the cases wherein $R_3$ is a substituent other than hydrogen and $R_1$ to $R_2$ and $R_4$ to $R_{11}$ are each a substituent other than hydrogen or a hydrogen atom (29 cases in total), (2-4) the cases wherein $R_4$ is a substituent other than hydrogen and $R_1$ to $R_3$ and $R_5$ to $R_{11}$ are each a substituent other than hydrogen or a hydrogen atom (29 cases in total), (2-5) the cases wherein $R_5$ is a substituent other than hydrogen and $R_1$ to $R_4$ and $R_7$ to $R_{11}$ are each a substituent other than hydrogen or a hydrogen atom (29 cases in total), (2-6) the cases wherein $R_7$ is a substituent other than hydrogen and $R_1$ to $R_5$ and $R_8$ to $R_{11}$ are each a substituent other than hydrogen or a hydrogen atom (29 cases in total), (2-7) the cases wherein $R_8$ is a substituent other than hydrogen and $R_1$ to $R_7$ and $R_9$ to $R_{11}$ are each a substituent other than hydrogen or a hydrogen atom (29 cases in total), (2-8) the cases wherein $R_9$ is a substituent other than hydrogen and $R_1$ to $R_8$, $R_{10}$ and $R_{11}$ are each a substituent other than hydrogen or a hydrogen atom (29 cases in total), (2-9) the cases wherein $R_{10}$ is a substituent other than hydrogen and $R_1$ to $R_9$ and $R_{11}$ are each a substituent other than hydrogen or a hydrogen atom (29 cases in total), and (2-10) the cases wherein $R_{11}$ is a substituent other than hydrogen and $R_1$ to $R_{10}$ are each a substituent other than hydrogen or a hydrogen atom (29 cases in total) may exist. The numbers of the above-mentioned cases include overlapped cases. Furthermore, $R_1$, $R_2$, $R_3$, $R_4$, $R_5$, $R_7$, $R_8$, $R_9$, $R_{10}$ and $R_{11}$ may respectively be the same substituent or different substituents.

Alternatively, in the photoelectric conversion element and the like according to the second embodiment of the present invention, a constitution wherein at least one of $R_3$ and $R_9$ is a substituent other than hydrogen and at least one of $R_1$, $R_4$, $R_5$, $R_7$, $R_{10}$ and $R_{11}$ is a substituent other than hydrogen can be formed. Alternatively, in the photoelectric conversion element and the like according to the second embodiment of the present invention, a constitution wherein at least one of $R_3$ and $R_9$ is a substituent other than hydrogen and at least one of $R_4$, $R_5$, $R_{10}$ and $R_{11}$ is a substituent other than hydrogen can be formed. In such preferable constitution, specifically, for example, (3-1) the cases wherein $R_3$ is a substituent other than hydrogen and $R_1$ and $R_4$ to $R_{11}$ are each a substituent other than hydrogen or a hydrogen atom (27 cases in total), (3-2) the cases wherein $R_9$ is a substituent other than hydrogen and $R_1$ to $R_7$, $R_{10}$ and $R_{11}$ are each a substituent other than hydrogen or a hydrogen atom (27 cases in total), (3-3) the cases wherein $R_3$ and $R_9$ are each a substituent other than hydrogen and $R_1$, $R_4$, $R_5$, $R_7$, $R_{10}$ and $R_{11}$ are each a substituent other than hydrogen or a hydrogen atom (26 cases in total), (3-4) the cases wherein $R_3$ is a substituent other than hydrogen, $R_1$ is a hydrogen atom and $R_4$ to $R_{11}$ are each a substituent other than hydrogen or a hydrogen atom (26 cases in total), (3-5) the cases wherein $R_3$ is a substituent other than hydrogen, $R_7$ is a hydrogen atom and $R_1$, $R_4$, $R_5$ and $R_9$ to $R_{11}$ are each a substituent other than hydrogen or a hydrogen atom (26 cases in total), (3-6) the cases wherein $R_9$ is a substituent other than hydrogen, $R_1$ is a hydrogen atom, and $R_3$ to $R_7$, $R_{10}$ and $R_{11}$ are each a substituent other than hydrogen or a hydrogen atom (26 cases in total), (3-7) the cases wherein $R_9$ is a substituent other than hydrogen, $R_7$ is a hydrogen atom, and $R_1$, $R_3$ to $R_5$, $R_{10}$ and $R_{11}$ are each a substituent other than hydrogen or a hydrogen atom (26 cases in total), (3-8) the cases wherein $R_3$ and $R_9$ are each a substituent other than hydrogen, $R_1$ is a hydrogen atom, and $R_4$ to $R_7$, $R_{10}$ and $R_{11}$ are each a substituent other than hydrogen or a hydrogen atom (25 cases in total), (3-9) the cases wherein $R_3$ and $R_9$ are each a substituent other than hydrogen, $R_7$ is a hydrogen atom, and $R_1$, $R_4$, $R_5$, $R_{10}$ and $R_{11}$ are each a substituent other than hydrogen or a hydrogen atom (25 cases in total), and (3-10) the cases wherein $R_3$ and $R_9$ are each a substituent other than hydrogen, $R_1$ and $R_7$ are each a hydrogen atom, and $R_4$, $R_5$, $R_{10}$ and $R_{11}$ are each a substituent other than hydrogen or a hydrogen atom (24 cases in total) may exist. The numbers of the above-mentioned cases include overlapped cases. Furthermore, $R_1$, $R_3$, $R_4$, $R_5$, $R_7$, $R_9$, $R_{10}$ and $R_{11}$ may respectively be the same substituent or different substituents.

As the alkyl group in the structural formula (1) or structural formula (2), a methyl group, an ethyl group, a propyl group, an isopropyl group, a tert-butyl group, a pentyl group, a hexyl group, an octyl group, a dodecyl group and the like can be exemplified. They may be a straight chain or branched. Furthermore, the cycloalkyl group can include a cyclopentyl group, a cyclohexyl group and the like; the alkenyl group can include a vinyl group and the like; the alkynyl group can include an ethynyl group and the like; the aryl group can include a phenyl group, a naphthyl group, a biphenyl group and the like; the arylalkyl group can include a methylaryl group, an ethylaryl group, an isopropylaryl group, a n-butylaryl group, a p-tolyl group, a p-ethylphenyl group, a p-isopropylphenyl group, a 4-propylphenyl group, a 4-butylphenyl group, 4-nonylphenyl group and the like; the aromatic heterocycle may include a pyridyl group, a thienyl group, a furyl group, a pyridazinyl group, a pyrimidinyl group, a pyrazinyl group, a triazinyl group, an imidazolyl group, a pyrazolyl group, a thiazolyl group, a quinazolinyl group, a phthalazinyl group and the like; the heterocycle group can include a pyrrolidyl group, an imidazolidyl group, a morpholyl group, an oxazolidyl group and the like; the alkoxy group can include a methoxy group, an ethoxy group, a propyloxy group, a pentyloxy group, a hexyloxy group and the like; the cycloalkoxy group can include a cyclopentyloxy group, a cyclohexyloxy group and the like; the aryloxy group can include a phenoxy group, a naphthyloxy group and the like; the alkylthio group can include a methylthio group, an ethylthio group, a propylthio group, a pentylthio group, a hexylthio group and the like;

the cycloalkylthio group can include a cyclopentylthio group, a cyclohexylthio group and the like; the arylthio group can include a phenylthio group, a naphthylthio group and the like; the alkoxycarbonyl group can include a methyloxycarbonyl group, an ethyloxycarbonyl group, a butyloxycarbonyl group, an octyloxycarbonyl group and the like; the aryloxycarbonyl group can include a phenyloxycarbonyl group, a naphthyloxycarbonyl group and the like; the sulfamoyl group can include an aminosulfonyl group, a methylaminosulfonyl group, a dimethylaminosulfonyl group, a cyclohexylaminosulfonyl group, a phenylaminosulfonyl group, a naphthylaminosulfonyl group, a 2-pyridylaminosulfonyl group and the like; the acyl group can include an acetyl group, an ethylcarbonyl group, a propylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, a pyridylcarbonyl group and the like; the thiocarbonyl group can include a thioacetyl group, an ethylthiocarbonyl group, a propylthiocarbonyl group, a cyclohexylthiocarbonyl group, an octylthiocarbonyl group, a 2-ethylhexylthiocarbonyl group, a dodedcylthiocarbonyl group, a phenylthiocarbonyl group, a naphthylthiocarbonyl group, a pyridylthiocarbonyl group and the like; the acyloxy group can include an acetyloxy group, an ethylcarbonyloxy group, an octylcarbonyloxy group, a phenylcarbonyloxy group and the like; the amide group can include a methylcarbonylamino group, an ethylcarbonylamino group, a dimethylcarbonylamino group, a pentylcarbonylamino group, a cyclohexylcarbonylamino group, a 2-ethylhexylcarbonylamino group, a phenylcarbonylamino group, a naphthylcarbonylamino group and the like; the carbamoyl group can include an aminocarbonyl group, a methylaminocarbonyl group, a dimethylaminocarbonyl group, a dimethylaminocarbonyl group, a 2-ethylhexylaminocarbonyl group, a phenylaminocarbonyl group, a naphthylaminocarbonyl group, a 2-pyridylaminocarbonyl group and the like; the ureido group can include a methylureido group, an ethylureido group, a cyclohexylureido group, a dodedcylureido group, a phenylureido group, a naphthylureido group, a 2-pyridylaminoureido group and the like; the sulfinyl group can include a methylsulfinyl group, an ethylsulfinyl group, a butylsulfinyl group, a cyclohexylsulfinyl group, a 2-ethylhexylsulfinyl group, a phenylsulfinyl group, a naphthylsulfinyl group, a 2-pyridylsulfinyl group and the like; the alkylsulfonyl group can include a methylsulfonyl group, an ethylsulfonyl group, a butylsulfonyl group, a cyclohexylsulfonyl group, a 2-ethylhexylsulfonyl group, a dodedcylsulfonyl group and the like; the arylsulfonyl group can include a phenylsulfonyl group, a naphthylsulfonyl group, a 2-pyridylsulfonyl group and the like; the amino group can include an amino group, an ethylamino group, a dimethylamino group, a butylamino group, a 2-ethylhexylamino group, an anilino group, a naphthylamino group, a 2-pyridylamino group and the like; the halogen atom may include a fluorine atom, a chlorine atom, a bromine atom and an iodine atom; and the fluorohydrocarbon group can include a fluoromethyl group, a trifluoromethyl group, a pentafluoroethyl group, a pentafluorophenyl group and the like. Furthermore, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group and a sulfo group can be exemplified, and the silyl group can include a trimethylsilyl group, a triisopropylsilyl group, a triphenylsilyl group, a phenyldiethylsilyl group and the like. The substituents exemplified above may further be substituted with the above-mentioned substituents. Furthermore, a plurality of these substituents may bind to each other to form a ring.

The solid-state imaging device of the present invention can be a surface irradiation type or a rear surface irradiation type, and can constitute a single plate color solid-state imaging device. In addition, where necessary, an on-chip micro lens and a shading layer may be disposed on the solid imaging sensor in the solid-state imaging device, and a driving circuit and wires for driving the photoelectric conversion element (solid imaging sensor) are disposed. Where necessary, a shutter for controlling the incidence of light into the photoelectric conversion element (solid imaging sensor) may be disposed, and the solid-state imaging device may comprise an optical cut filter according to its purpose. Furthermore, in the case when the solid imaging sensor in the solid-state imaging device is constituted by a single layer of the photoelectric conversion element of the present invention, examples of the array of the photoelectric conversion element may include a Bayer array, an interline array, a G stripe-RB checkered array, a G stripe-RB full-checkered array, a checkered complementary color array, a stripe array, a diagonal stripe array, a primary color difference array, a field color difference sequential array, a flame color difference sequential array, an MOS-type array, a modified MOS-type array, a flame interleave array and a field interleave array. Meanwhile, according to the photoelectric conversion element of the present invention, imaging devices (solid-state imaging devices) such as television cameras, as well as optical sensors, image sensors and solar cells can be constituted.

Example 1

Example 1 relates to the photoelectric conversion elements and solid-state imaging devices of the first embodiment and second embodiment of the present invention. As shown by a schematic partial cross-sectional view in FIG. 1, a photoelectric conversion element 11 in Example 1 comprises (a-1) a first electrode 21 and a second electrode 22 which are disposed apart from each other, and (a-2) a photoelectric conversion material layer 30 that is disposed between the first electrode 21 and the second electrode 22. More specifically, the first electrode 21 formed of a transparent electroconductive material is formed on a transparent substrate 20, a photoelectric conversion material layer 30 is formed on the first electrode 21, and the second electrode 22 is formed on the photoelectric conversion material layer 30.

The first electrode 21 that is an electrode at the light incidence side is formed of a transparent electroconductive material, specifically, indium-tin oxide (ITO) having a thickness of 120 nm. The second electrode 22 is formed of aluminum (Al) having a thickness of 100 nm. The first electrode 21 formed of a transparent electroconductive material is formed on the transparent substrate 20, the photoelectric conversion material layer 30 is formed on the first electrode 21, and the second electrode 22 is formed on the photoelectric conversion material layer 30. Light enters the photoelectric conversion material layer 30 through the substrate 20 and first electrode 21. The substrate 20 is formed of a quartz substrate having a thickness of 0.7 mm. The first electrode 21 at the side of the photoelectric conversion material layer had a surface roughness $R_a$ of 0.28 nm and $R_{max}$ of 3.3 nm. Generally, it is desirable that the first electrode 21 has a surface roughness $R_a$ of 1.0 nm or less, preferably 0.3 nm or less.

Furthermore, the photoelectric conversion material layer 30 is formed of the dioxaanthanthrene-based compound represented by the above-mentioned structural formula (1) [the first embodiment of the present invention] or the structural formula (2) [the second embodiment of the present invention]. In Example 1, more specifically, the photoelectric conversion material layer 30 is formed of a dioxaanthanthrene-based compound represented by the structural formula (3), i.e., 3,9-bis(p-ethylphenyl)peri-xanthenoxanthene represented as "PXX—(C2Ph)$_2$" and absorbs lights from blue to green. R$_3$ and R$_9$ are each constituted by an arylalkyl group (an aryl group partially substituted with alkyl group(s). The same applies to the following descriptions.)

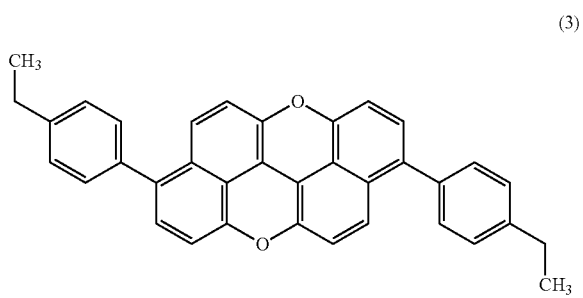 [SMILES: CCc1ccc(-c2ccc3oc4ccc5c(-c6ccc(CC)cc6)ccc6oc7ccc2c3c7-c4c65)cc1]

(3)

In other words, the dioxaanthanthrene-based compound of Example 1 is obtained by halogenating peri-xanthenoxanthene to give 3,9-dihalo-peri-xanthenoxanthene, and substituting the halogen atom(s) with substituent(s), and is formed by substituting at least one of the 3- and 9-positions of 6,12-dioxaanthanthrene with the substituent(s) other than hydrogen. The halogen atoms are specifically bromine (Br). Furthermore, the substituents are each formed of an aryl group or an arylalkyl group, or the substituents are each formed of an aryl group in which at least one of 2- to 6-positions is substituted with an alkyl group, or an aryl group in which at least one of 2- to 6-positions is substituted with an aryl group. The same also applies to Examples 2 to Example 12 mentioned below.

Specifically, the dioxaanthanthrene-based compound of Example 1 can be obtained by reacting peri-xanthenoxanthene with bromine to give 3,9-dibromo-peri-xanthenoxanthene, and substituting the bromine atoms with p-ethylphenyl groups. Namely, PXX—(C2Ph)$_2$, which is the dioxaanthanthrene-based compound of Example 1, can be synthesized based on the following scheme.

Figure 2:
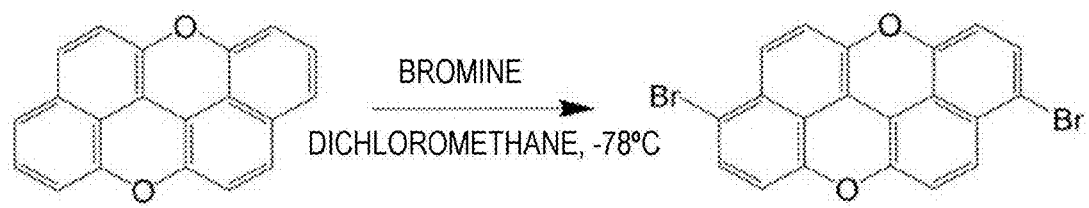
FIG. 2 is a drawing that illustrates a part of the synthesis scheme of 3,9-bis(p-ethylphenyl)peri-xanthenoxanthene.

First, as shown in the scheme in FIG. 2, a bromide of PXX, PXX—Br$_2$ is synthesized. Specifically, a dichloromethane solution of PXX (1 equivalent amount) was reacted with a dichloromethane solution of bromine (2 equivalent amount) at −78° C. Thereafter the temperature of the reaction liquid was returned to room temperature, and the reaction liquid was treated with an aqueous solution of sodium hydrogen sulfite to give a yellow-green crude product. Furthermore, the crude product collected by filtration was washed with dichloromethane to give 3,9-dibromo-peri-xanthenoxanthene (PXX—Br$_2$). This could be confirmed to be a dibromide by a Time-of-flight Mass Spectrometry (abbreviated as "Tof-MS") and 1H-NMR (proton nuclear magnetic resonance spectrometry).

Next, a catalytic amount of tetrakistriphenylphosphine palladium(0) was added to a toluene solution of PXX—Br$_2$ (1 equivalent amount) and p-ethylphenylboronic acid (2 equivalent amount) in the presence of sodium carbonate, and reflux was conducted for 48 hours. The reaction liquid was then allowed to cool to room temperature and poured into methanol, and the precipitated yellow solid was collected by filtration and washed with methanol, hydrochloric acid and water. Recrystallization from tetrahydrofuran was then conducted to give a yellow needle crystal.

It could be confirmed by Tof-MS and 1H-NMR that the crystal was a di-substituted form, 3,9-bis(p-ethylphenyl)peri-xanthenoxanthene [PXX—(C2Ph)$_2$].

The photoelectric conversion element 11 of Example 1 was prepared by the following process. Namely, the first electrode 21 formed of ITO having a thickness of 120 nm is formed on the substrate 20 based on a lithography technique using a photomask. Next, a convex portion 31 formed of an insulating material was formed on the substrate 20 and the first electrode 21, thereafter the photoelectric conversion material layer 30 formed of the dioxaanthanthrene-based compound of the above-mentioned structural formula (1), (2) or (3) (thickness 100 nm) was formed (film formation) throughout from the first electrode 21 to the convex portion 31 by a vacuum deposition process based on a vacuum deposition process using a metal mask. The substrate temperature during the vacuum deposition was 110° C., and the film forming velocity of the photoelectric conversion material layer 30 was 0.1 nm/sec. Next, the second electrode 22 formed of aluminum having a thickness of 100 nm was formed throughout from the photoelectric conversion material layer 30 to the substrate 20 by a PVD process using a metal mask. As the conditions for the formation of the second electrode 22, the substrate temperature was 30° C., and the film formation velocity of the second electrode 22 was 0.5 nm/sec. The convex portion 31 is formed so as to surround the area of the substrate 20 on which the photoelectric conversion material layer 30 is to be formed. Furthermore, prior to the film-formation of the photoelectric conversion material layer 30, the first electrode 21 as a primer and the convex portion 31 were subjected to an UV ozone treatment. Also in Example 2 to Example 14 mentioned below, photoelectric conversion elements can be prepared in a similar manner.

Figure 3:
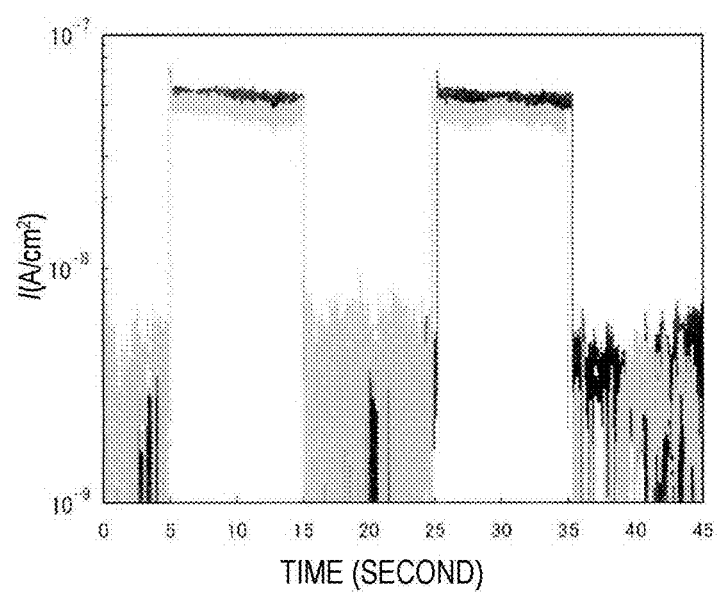
FIG. 3 is a graph showing the on-off response property of the photocurrent obtained by the presence or absence of light at a wavelength of 428 nm in the photoelectric conversion element of Example 1.

The on-off response property of the photocurrent obtained by the presence or absence of irradiation of light at a wavelength of 428 nm in the photoelectric conversion element 11 of Example 1 as obtained is shown in FIG. 3. The photocurrent showed saturation within 5 milliseconds from the time of light irradiation, and the current value decreased immediately when the light irradiation was stopped, and thus it is found that the light responsiveness is quick. In addition, also in the respective Examples mentioned below, although the wavelength of the light that was irradiated depending on the dioxaanthanthrene-based compound used was different, the on-off response of the photocurrent was obtained depending on the presence or absence of light irradiation as in Example 1; furthermore, since the photocurrent showed saturation immediately after the time of light irradiation, and the current value quickly decreased when light irradiation was stopped, it was found that the light responsiveness was quick.

Figure 4:
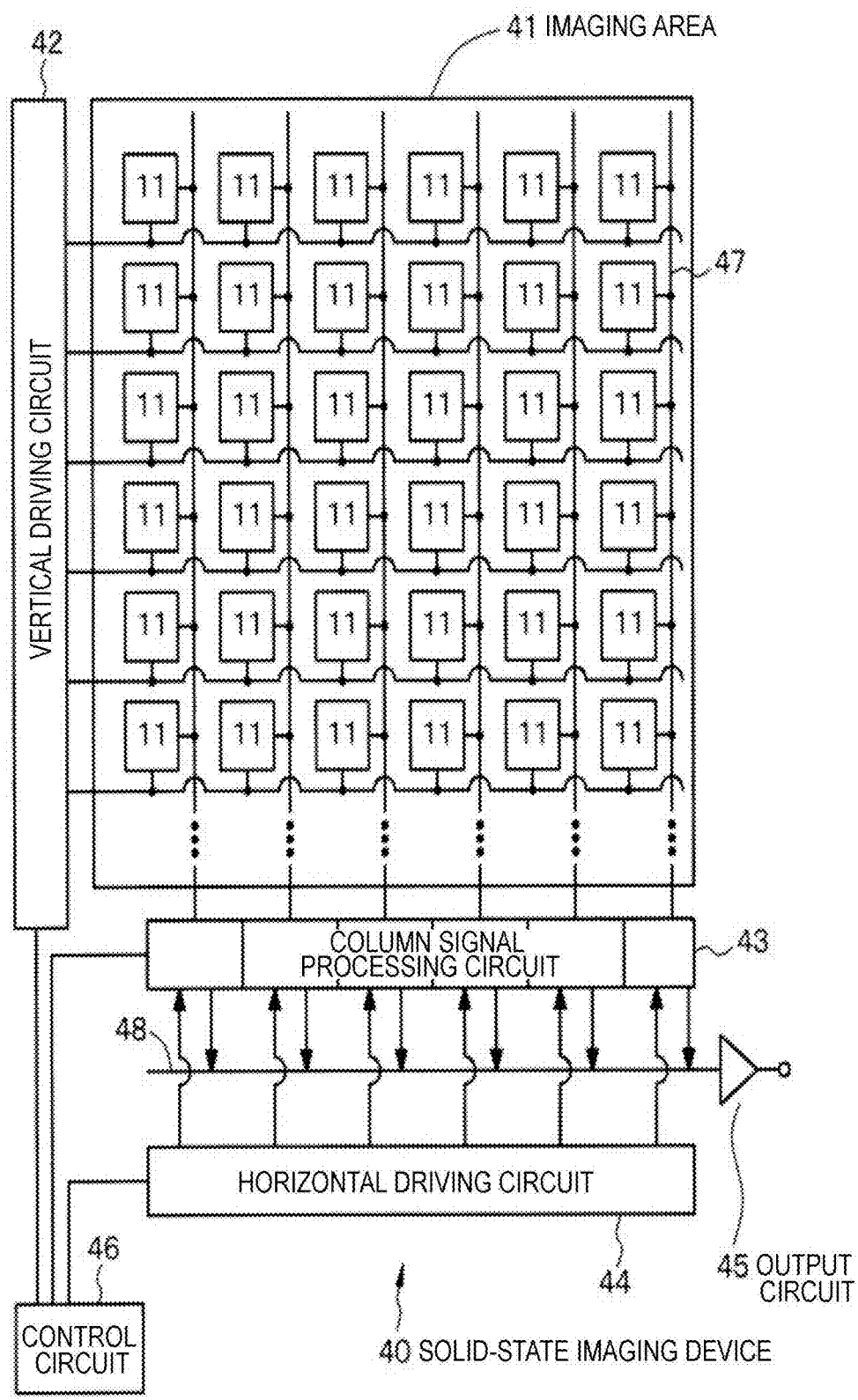
FIG. 4 is a conceptual drawing of the solid-state imaging device of Example 1.

FIG. 4 shows a conceptual drawing of the solid-state imaging device (solid imaging sensor) of Example 1. Also in Example 2 to Example 14 mentioned below, the solid-state imaging device (solid imaging sensor) has similar constitution and structure to those of the solid-state imaging device (solid imaging sensor) of Example 1. The solid-state imaging device 40 of Example 1 is constituted by an imaging area 41 in which the above-mentioned photoelectric conversion elements 11 are disposed in a two-dimensional array on a semiconductor substrate (for example, an Si substrate), and a vertical driving circuit 42, a column signal processing circuit 43, a horizontal driving circuit 44, an output circuit 45 and a control circuit 46 as peripheral circuits therefor, and the like.

It is needless to say that these circuits can be constituted by well-known circuits, or can be constituted by using other circuit constitutions (for example, various circuits used in conventional CCD imaging devices and CMOS imaging devices).

The control circuit 46 generates a clock signal and a control signal that form the basis for the operations of the vertical driving circuit 42, column signal processing circuit 43 and horizontal driving circuit 44, based on a vertical synchronizing signal, a horizontal synchronizing signal and a master clock. Furthermore, the clock signal and control signal generated are input to the vertical driving circuit 42, column signal processing circuit 43 and horizontal driving circuit 44.

The vertical driving circuit 42 is constituted by, for example, a shift register, and selectively scans the respective photoelectric conversion elements 11 on the imaging area 41 sequentially in increments of lines in the vertical direction. Furthermore, a pixel signal based on a current (signal) generated depending on the amount of the received light in each photoelectric conversion element 11 is sent to the column signal processing circuit 43 through a vertical signal line 47.

The column signal processing circuit 43 is disposed, for example, on every row of the photoelectric conversion elements 11, and conducts noise removal and a signal processing for signal amplification on every photoelectric conversion element on the signals that are output from the photoelectric conversion elements 11 on one line, by signals from black-based pixels (these are not depicted, but are formed around an effective pixel area). A horizontal selection switch (not depicted) is disposed by connecting with the horizontal signal line 48 on the output stage of the column signal processing circuit 43.

The horizontal driving circuit 44 is constituted by, for example, a shift register, and sequentially selects each column signal processing circuit 43 by sequentially outputting horizontal scanning pulses, and outputs a signal from each column signal processing circuit 43 to the horizontal signal line 48.

The output circuit 45 conducts signal processes on the signals that are sequentially fed from the respective column signal processing circuits 43 via the horizontal signal line 48, and outputs the signals.

Example 2

Example 2 is a modification of Example 1. In Example 2, 3,9-diphenyl-peri-xanthenoxanthene represented by the following structural formula (4) (represented as "PXX-Ph$_2$") was used as the dioxaanthanthrene-based compound. Namely, the dioxaanthanthrene-based compound of Example 2 is formed of 3,9-diphenyl-peri-xanthenoxanthene obtained by reacting peri-xanthenoxanthene with bromine to give 3,9-dibromo-peri-xanthenoxanthene, and substituting the bromine with phenyl groups. $R_3$ and $R_9$ are each an aryl group (specifically a phenyl group), and lights from blue to green are absorbed.

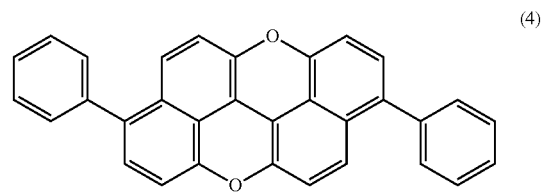 [SMILES: c1ccc(-c2ccc3oc4ccc5c(-c6ccccc6)ccc6oc7ccc2c3c7-c4c65)cc1]

(4)

The dioxaanthanthrene-based compound of Example 2 [PXX-Ph$_2$] could be obtained through a similar scheme to that of Example 1, except that p-ethylphenylboronic acid in the synthesis of Example 1 was changed to (4,4,5,5-tetramethyl-1,3,2-dioxaborolan-2-yl)benzene. It could be confirmed by Tof-MS and 1H-NMR that the compound was a di-substituted form, [PXX-Ph$_2$].

Example 3

Example 3 is also a modification of Example 1. In Example 3, 3,9-di(trans-1-octen-1-yl)peri-xanthenoxanthene represented by the following structural formula (5) (represented as "PXX—(VC6)$_2$") was used as the dioxaanthanthrene-based compound. Namely, the dioxaanthanthrene-based compound of Example 3 is formed of 3,9-di(trans-1-octen-1-yl)peri-xanthenoxanthene obtained by reacting peri-xanthenoxanthene with bromine to give 3,9-dibromo-peri-xanthenoxanthene, and substituting the bromine atoms with trans-1-octen-1-yl groups. $R_3$ and $R_9$ are each constituted by an alkenyl group (specifically a vinyl group) and an alkyl group, and lights from blue to green are absorbed.

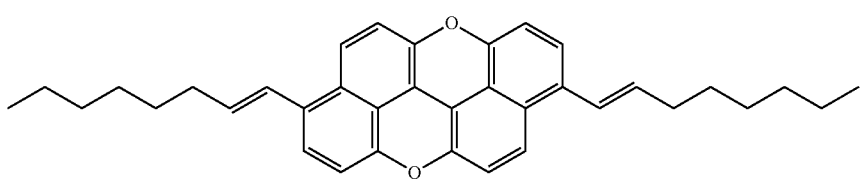

(5)

The PXX—(VC6)$_2$ of Example 3 could be obtained through a similar scheme to that of Example 1, except that p-ethylphenylboronic acid in the synthesis of Example 1 was changed to trans-1-octen-1-ylboronic acid pinacol ester. Furthermore, purification was conducted by recrystallization from toluene. It could be confirmed by Tof-MS and 1H-NMR that the compound was a di-substituted form, PXX—(VC6)$_2$.

Example 4

Example 4 is also a modification of Example 1. In Example 4, 3,9-di(2-naphthyl)peri-xanthenoxanthene represented by the following structural formula (6) (represented as "PXX—(Nap)$_2$") was used as the dioxaanthanthrene-based compound. Namely, the dioxaanthanthrene-based compound of Example 4 is formed of 3,9-di(2-naphthyl)peri-xanthenoxanthene obtained by reacting peri-xanthenoxanthene with bromine to give 3,9-dibromo-peri-xanthenoxanthene, and substituting the bromine atoms with β-naphthyl groups. $R_3$ and $R_9$ are each an aryl group (specifically a β-naphthyl group), and lights from blue to green are absorbed.

(6)

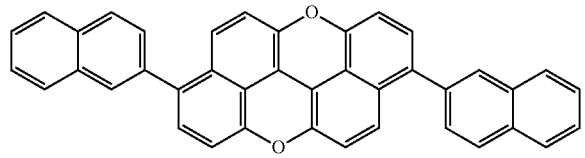

(8)

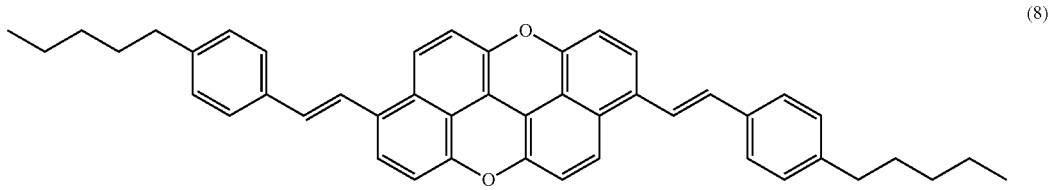 [SMILES: CCCCCc1ccc(/C=C/c2ccc3oc4ccc5c(/C=C/c6ccc(CCCCC)cc6)ccc6oc7ccc2c3c7-c4c65)cc1]

The PXX—(Nap)₂ of Example 4 could be obtained through a similar scheme to that of Example 1, except that p-ethylphenylboronic acid in the synthesis of Example 1 was changed to naphthalene-2-boronic acid pinacol ester. Furthermore, purification was conducted by extraction using tetrahydrofuran. It could be confirmed by Tof-MS and 1H-NMR that the compound was a di-substituted form, PXX—(Nap)₂.

Example 5

Example 5 is also a modification of Example 1. In Example 5, 3,9-bis(2,2'-bithiophen-5-yl)peri-xanthenoxanthene represented by the following structural formula (7) (represented as "PXX—(BT)₂") was used as the dioxaanthanthrene-based compound. Namely, the dioxaanthanthrene-based compound of Example 5 is formed of 3,9-bis(2,2'-bithiophen-5-yl)peri-xanthenoxanthene obtained by reacting peri-xanthenoxanthene with bromine to give 3,9-dibromo-peri-xanthenoxanthene, and substituting the bromine atoms with 2,2'-bithiophen-5-yl groups. R₃ and R₉ are each an aromatic heterocycle group (specifically a 2,2'-bithiophen-5-yl group), and lights from blue to green are absorbed.

(7)

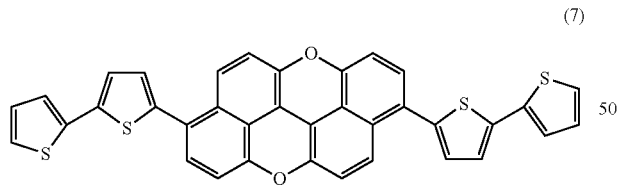

The PXX—(Nap)₂ of Example 5 could be obtained through a similar scheme to that of Example 1, except that p-ethylphenylboronic acid in the synthesis of Example 1 was changed to 2,2'-bithiophen-5-boronic acid pinacol ester. Furthermore, purification was conducted by extraction using tetrahydrofuran. It could be confirmed by Tof-MS and 1H-NMR that the compound was a di-substituted form, PXX—(BT)₂.

Example 6

Example 6 is also a modification of Example 1. In Example 6, 3,9-bis(trans-2-(4-pentylphenyl)vinyl)peri-xanthenoxanthene represented by the following structural formula (8) (represented as "PXX—(VPC5)₂") was used as the dioxaanthanthrene-based compound. Namely, the dioxaanthanthrene-based compound of Example 6 is formed of 3,9-bis(trans-2-(4-pentylphenyl)vinyl)peri-xanthenoxanthene obtained by reacting peri-xanthenoxanthene with bromine to give 3,9-dibromo-peri-xanthenoxanthene, and substituting the bromine atoms with trans-2-(4-pentylphenyl)vinyl groups. R₃ and R₉ are each constituted by a vinyl group, a phenyl group and an alkyl group, and lights from blue to green are absorbed.

The PXX—(VPC5)₂ of Example 6 could be obtained through a similar scheme to that of Example 1, except that p-ethylphenylboronic acid in the synthesis of Example 1 was changed to 2-[2-(4-pentylphenyl)vinyl]-4,4,5,5-tetramethyl-1,3,2-dioxaborolane. Furthermore, purification was conducted by extraction using tetrahydrofuran. It could be confirmed by Tof-MS and 1H-NMR that the compound was a di-substituted form, PXX—(VPC5)₂.

Example 7

Example 7 is also a modification of Example 1. In Example 7, 3,9-di(p-tolyl)peri-xanthenoxanthene represented by the following structural formula (9) (represented as "PXX—(C1Ph)₂") was used as the dioxaanthanthrene-based compound. Namely, the dioxaanthanthrene-based compound of Example 7 is formed of 3,9-di(p-tolyl)peri-xanthenoxanthene obtained by reacting peri-xanthenoxanthene with bromine to give 3,9-dibromo-peri-xanthenoxanthene, and substituting the bromine atoms with p-tolyl groups. R₃ and R₉ are each constituted by an arylalkyl group, and lights from blue to green are absorbed.

(9)

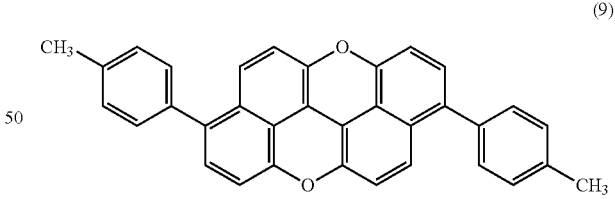

The PXX—(C1Ph)₂ of Example 7 could be obtained through a similar scheme to that of Example 1, except that p-ethylphenylboronic acid in the synthesis of Example 1 was changed to p-tolylboronic acid. Furthermore, sublimation was conducted under high vacuum, and thereafter purification was conducted by extraction by using tetrahydrofuran. It could be confirmed by Tof-MS that the compound was a di-substituted form, PXX—(C1Ph)₂.

Example 8

Example 8 is also a modification of Example 1. In Example 8, 3,9-bis(p-isopropylphenyl)peri-xanthenoxanthene represented by the following structural formula (10) (represented as "PXX-(iC3Ph)$_2$") was used as the dioxaanthanthrene-based compound. Namely, the dioxaanthanthrene-based compound of Example 8 is formed of 3,9-bis(p-isopropylphenyl)peri-xanthenoxanthene obtained by reacting peri-xanthenoxanthene with bromine to give 3,9-dibromo-peri-xanthenoxanthene, and substituting the bromine atoms with p-isopropylphenyl groups. R$_3$ and R$_9$ are each constituted by an arylalkyl group, and lights from blue to green are absorbed.

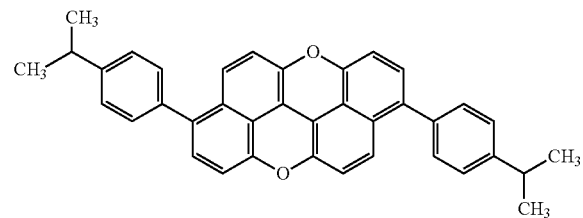

(10)

The PXX-(iC3Ph)$_2$ of Example 8 could be obtained through a similar scheme to that of Example 1, except that p-ethylphenylboronic acid in the synthesis of Example 1 was changed to p-isopropylphenylboronic acid. Furthermore, sublimation was conducted under high vacuum, and thereafter purification was conducted by recrystallization using toluene. It could be confirmed by Tof-MS and 1H-NMR that the compound was a di-substituted form, PXX-(iC3Ph)$_2$.

Example 9

Example 9 is also a modification of Example 1. In Example 9, 3,9-bis(4-propylphenyl)peri-xanthenoxanthene represented by the following structural formula (11) (represented as "PXX—(C$_3$Ph)$_2$") was used as the dioxaanthanthrene-based compound. Namely, the dioxaanthanthrene-based compound of Example 9 is formed of 3,9-bis(4-propylphenyl)peri-xanthenoxanthene obtained by reacting peri-xanthenoxanthene with bromine to give 3,9-dibromo-peri-xanthenoxanthene, and substituting the bromine atoms with 4-propylphenyl groups. R$_3$ and R$_9$ are each constituted by an arylalkyl group, and lights from blue to green are absorbed.

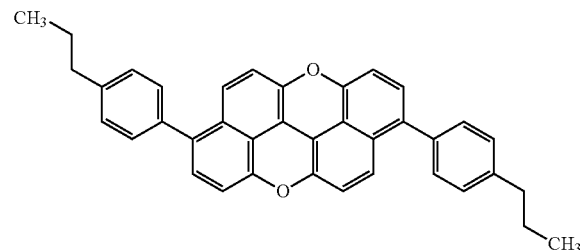

(11)

The PXX—(C3Ph)$_2$ of Example 9 could be obtained through a similar scheme to that of Example 1, except that p-ethylphenylboronic acid in the synthesis of Example 1 was changed to 4-propylphenylboronic acid. Furthermore, sublimation was conducted under high vacuum, and thereafter purification was conducted by recrystallization using toluene. It could be confirmed by Tof-MS and 1H-NMR that the compound was a di-substituted form, PXX—(C3Ph)$_2$.

Example 10

Example 10 is also a modification of Example 1. In Example 10, 3,9-bis(4-butylphenyl)peri-xanthenoxanthene represented by the following structural formula (12) (represented as "PXX—(C4Ph)$_2$") was used as the dioxaanthanthrene-based compound. Namely, the dioxaanthanthrene-based compound of Example 10 is formed of 3,9-bis(4-butylphenyl)peri-xanthenoxanthene obtained by reacting peri-xanthenoxanthene with bromine to give 3,9-dibromo-peri-xanthenoxanthene, and substituting the bromine atoms with 4-butylphenyl groups. R$_3$ and R$_9$ are each constituted by an arylalkyl group, and lights from blue to green are absorbed.

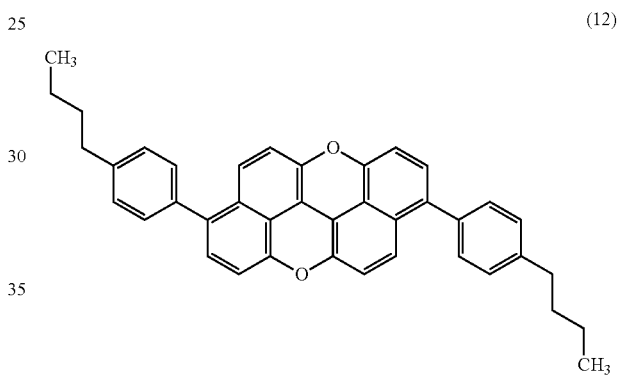

(12)

The PXX—(C4Ph)$_2$ of Example 10 could be obtained through a similar scheme to that of Example 1, except that p-ethylphenylboronic acid in the synthesis of Example 1 was changed to 4-butylphenylboronic acid. Furthermore, sublimation was conducted under high vacuum, and thereafter purification was conducted by extraction by toluene. It could be confirmed by Tof-MS and 1H-NMR that the compound was a di-substituted form, PXX—(C4Ph)$_2$.

Example 11

Example 11 is also a modification of Example 1. In Example 11, 3,9-bis(4-nonylphenyl)peri-xanthenoxanthene represented by the following structural formula (13) (represented as "PXX—(C9Ph)$_2$") was used as the dioxaanthanthrene-based compound. Namely, the dioxaanthanthrene-based compound of Example 11 is formed of 3,9-bis(4-nonylphenyl)peri-xanthenoxanthene obtained by reacting peri-xanthenoxanthene with bromine to give 3,9-dibromo-peri-xanthenoxanthene, and substituting the bromine atoms with 4-nonylphenyl groups. R$_3$ and R$_9$ are each constituted by an arylalkyl group, and lights from blue to green are absorbed.

(13)

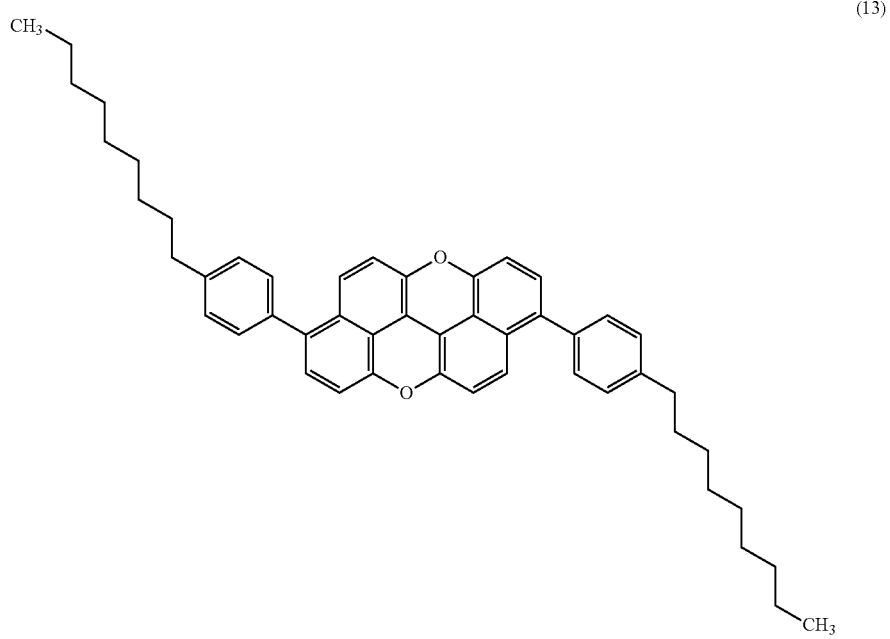 [SMILES: CCCCCCCCCc1ccc(-c2ccc3oc4ccc5c(-c6ccc(CCCCCCCCC)cc6)ccc6oc7ccc2c3c7-c4c65)cc1]

The PXX—(C9Ph)$_2$ of Example 11 could be obtained through a similar scheme to that of Example 1, except that p-ethylphenylboronic acid in the synthesis of Example 1 was changed to 4-n-nonylbenzeneboronic acid. Furthermore, sublimation was conducted under high vacuum, and thereafter purification was conducted by extraction by toluene. It could be confirmed by Tof-MS that the compound was a di-substituted form, PXX—(C9Ph)$_2$.

Example 12

Example 12 is also a modification of Example 1. In Example 12, 3,9-bis(p-biphenyl)peri-xanthenoxanthene represented by the following structural formula (14) (represented as "PXX—(BPh)$_2$") was used as the dioxaanthanthrene-based compound. Namely, the dioxaanthanthrene-based compound of Example 12 is formed of 3,9-di(p-biphenyl)peri-xanthenoxanthene obtained by reacting peri-xanthenoxanthene with bromine to give 3,9-dibromo-peri-xanthenoxanthene, and substituting the bromine atoms with p-biphenyl groups. R$_3$ and R$_9$ are each constituted by an aryl group, and lights from blue to green are absorbed.

(14)

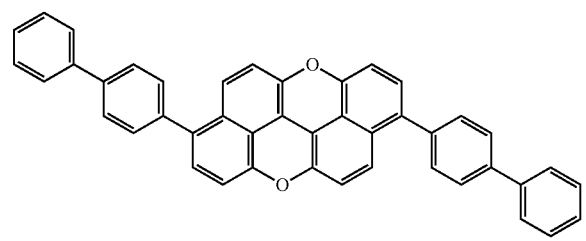

The PXX—(BPh)$_2$ of Example 12 could be obtained through a similar scheme to that of Example 1, except that p-ethylphenylboronic acid in the synthesis of Example 1 was changed to 4-biphenylboronic acid. Furthermore, sublimation was conducted under high vacuum, and thereafter purification was conducted by extraction by using benzene. It could be confirmed by Tof-MS that the compound was a di-substituted form, PXX—(BPh)$_2$.

Example 13

Figure 5:
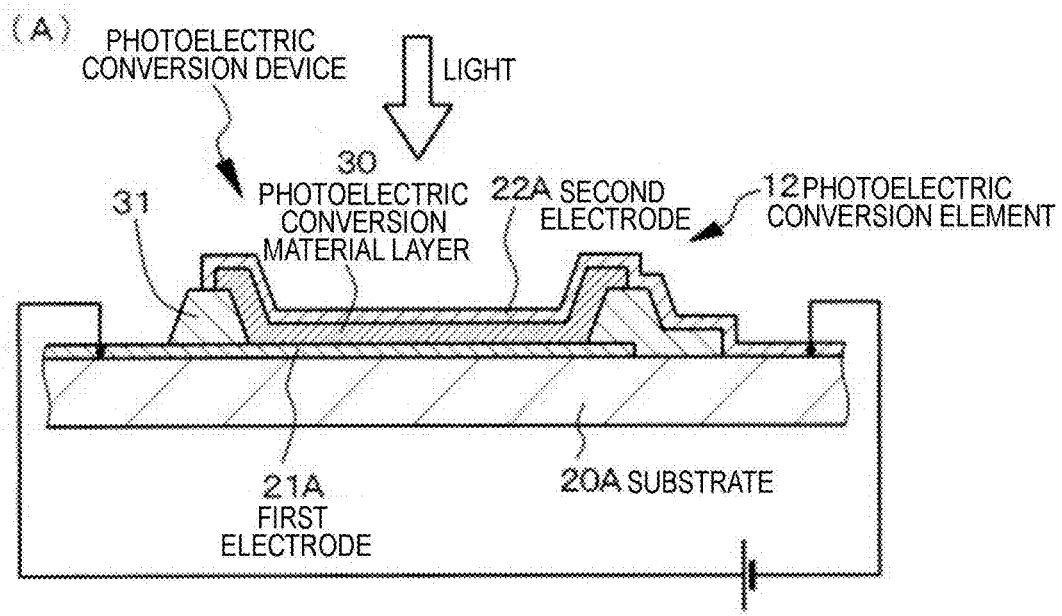
FIGS. 5(A) and 5(B) show schematic cross-sectional views of the photoelectric conversion elements of Example 13 and Example 14.
Figure 5:
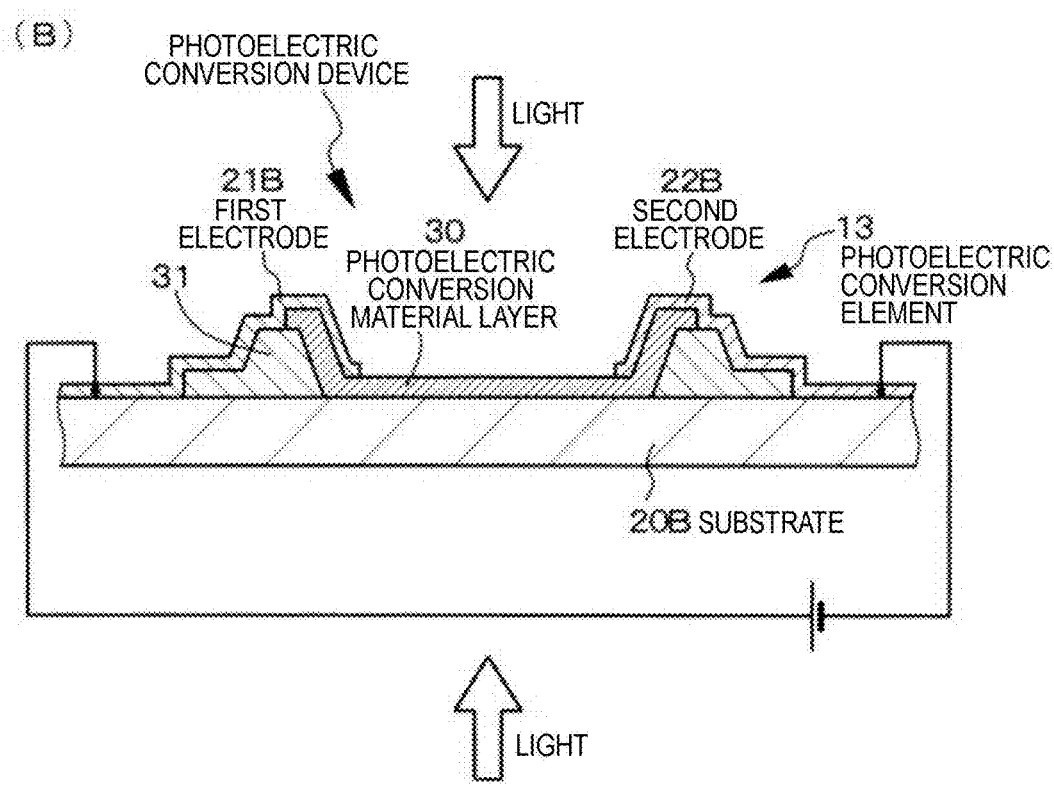

Example 13 is a modification of the photoelectric conversion element of Example 1. In the photoelectric conversion element 12 of Example 13, as shown by a schematic partial cross-sectional view in FIG. 5(A), a first electrode 21A is formed on a substrate 20A, a photoelectric conversion material layer 30 is formed on the first electrode 21A, and a second electrode 22A formed of a transparent electroconductive material is formed on the photoelectric conversion material layer 30. Light enters the photoelectric conversion material layer 30 through the second electrode 22A. Specifically, the substrate 20A is formed of, for example, a silicon semiconductor substrate, the first electrode 21A is formed of aluminum, and the second electrode 22A is formed of ITO. Except for this point, the constitution and structure of the photoelectric conversion element 12 of Example 13 can be similar to the constitution and structure of the photoelectric conversion element 11 of Example 1, and thus a detailed explanation is omitted.

Example 14

Example 14 is also a modification of the photoelectric conversion element of Example 1. In a photoelectric conversion element 13 of Example 14, as shown by a schematic partial cross-sectional view in FIG. 5(B), a first electrode 21B and a second electrode 22B are formed on a substrate, and a photoelectric conversion material layer 30 is formed on a substrate 20B throughout from the first electrode 21B to the second electrode 22B. Light enters the photoelectric conversion material layer 30 through the second electrode 22B.

Alternatively, light enters the photoelectric conversion material layer 30 through the substrate 20B and the first electrode 21B. Specifically, the substrate 20B is formed of, for example, a silicon semiconductor substrate, and the first electrode 21B and the second electrode 22B are formed of a metal material or a transparent electroconductive material. Except for this point, the constitution and structure of the photoelectric conversion element 13 of Example 14 can be similar to the constitution and structure of the photoelectric conversion element 11 of Example 1, and thus a detailed explanation is omitted.

The present invention has been explained above based on the preferable examples, but the present invention is not construed to be limited to these examples. The photoelectric conversion elements, the structures and constitutions of the solid-state imaging devices, the production conditions, the production processes, and the materials used as explained in Examples are for exemplification and can be suitably changed. The photoelectric conversion material layer may be constituted by one kind of dioxaanthanthrene-based compound, or may be constituted by a mixed product of plural kinds of dioxaanthanthrene-based compounds. Alternatively, the photoelectric conversion material layer may be formed of multiple layers, and the respective photoelectric conversion material layers may be constituted by different dioxaanthanthrene-based compounds. Alternatively, a solid-state imaging device having a structure in which photoelectric conversion elements (light receiving areas) are laminated, i.e., a structure in which subpixels are laminated can be obtained by disposing the photoelectric conversion element as explained in Example 1, for example, on a silicon semiconductor substrate, and disposing one or plural (for example, two) layer(s) of photoelectric conversion area(s) inside of the silicon semiconductor substrate that is positioned below the photoelectric conversion element. In such solid-state imaging device, blue light can be received, for example, by the photoelectric conversion element as explained in Example 1, and light(s) of the other color(s) can be received by disposing one or plural layer(s) of photoelectric conversion area(s) inside of the silicon semiconductor substrate. In addition, instead of disposing the photoelectric conversion area(s) inside of the silicon semiconductor substrate, the photoelectric conversion area(s) can be formed on the semiconductor substrate by an epitaxial growth process, or can be formed on a silicon layer in so-called an SOI structure. In the case when the photoelectric conversion element of the present invention is to be functioned as a solar cell, it is only necessary to irradiate the photoelectric conversion material layer with light in a state that a voltage is not applied to the gap between the first electrode and second electrode.

REFERENCE SIGNS LIST

11 . . . photoelectric conversion element, 20 . . . substrate, 21 . . . first electrode, 22 . . . second electrode, 30 . . . photoelectric conversion material layer, 31 . . . convex portion, 40 . . . solid-state imaging device, 41 . . . imaging area, 42 . . . vertical driving circuit, 43 . . . column signal processing circuit, 44 . . . horizontal driving circuit, 45 . . . output circuit, 46 . . . control circuit, 47 . . . vertical signal line, 48 . . . horizontal signal line

The invention claimed is:

1. A photoelectric conversion element, comprising:
(a-1) a first electrode and a second electrode which are disposed apart from each other; and
(a-2) a photoelectric conversion material layer that is disposed between the first electrode and the second electrode,
wherein the photoelectric conversion material layer is formed of a dioxaanthanthrene-based compound represented by the following structural formula (1):

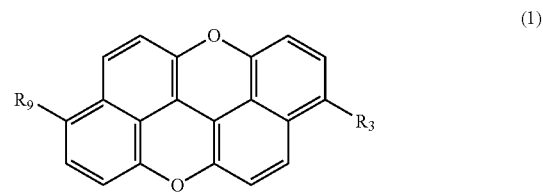

(1)

where at least one of $R_3$ and $R_9$ is a substituent other than hydrogen, and
the substituent other than hydrogen is a substituent selected from the group consisting of an alkyl group, a cycloalkyl group, an alkenyl group, an alkynyl group, an aryl group, an arylalkyl group, an aromatic heterocycle, a heterocycle group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, an ureido group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group and a silyl group.

2. A photoelectric conversion element, comprising:
(a-1) a first electrode and a second electrode which are disposed apart from each other; and
(a-2) a photoelectric conversion material layer that is disposed between the first electrode and the second electrode,
wherein the photoelectric conversion material layer is formed of a dioxaanthanthrene-based compound represented by the following structural formula (2):

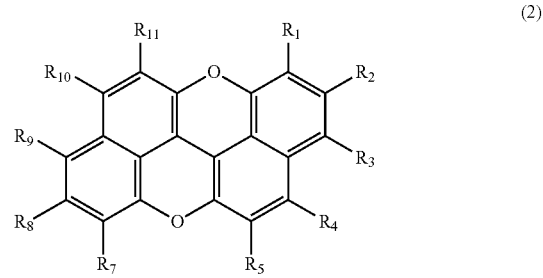

(2)

where at least one of $R_1$ to $R_{11}$ is a substituent other than hydrogen, and
the substituent other than hydrogen is a substituent selected from the group consisting of an alkyl group, a cycloalkyl group, an alkenyl group, an alkynyl group, an aryl group, an arylalkyl group, an aromatic heterocycle, a heterocycle group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, an ureido group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group and a silyl group.

3. The photoelectric conversion element according to claim 1 or 2, wherein the electrode on a light incident side is formed of a transparent electroconductive material.

4. A solid-state imaging device comprising a photoelectric conversion element comprising:
(a-1) a first electrode and a second electrode which are disposed apart from each other; and
(a-2) a photoelectric conversion material layer that is disposed between the first electrode and the second electrode,
wherein the photoelectric conversion material layer is formed of a dioxaanthanthrene-based compound represented by the following structural formula (1):

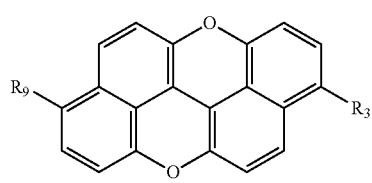

(1)

where at least one of $R_3$ and $R_9$ is a substituent other than hydrogen, and
the substituent other than hydrogen is a substituent selected from the group consisting of an alkyl group, a cycloalkyl group, an alkenyl group, an alkynyl group, an aryl group, an arylalkyl group, an aromatic heterocycle, a heterocycle group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, an ureido group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group and a silyl group.

5. A solid-state imaging device comprising a photoelectric conversion element comprising:
(a-1) a first electrode and a second electrode which are disposed apart from each other; and
(a-2) a photoelectric conversion material layer that is disposed between the first electrode and the second electrode,
wherein the photoelectric conversion material layer is formed of a dioxaanthanthrene-based compound represented by the following structural formula (2):

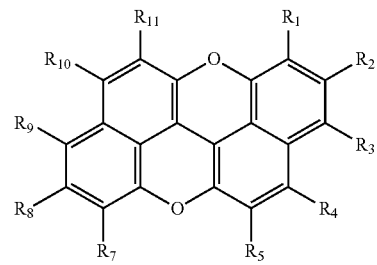

(2)

where at least one of $R_1$ to $R_{11}$ is a substituent other than hydrogen, and
the substituent other than hydrogen is a substituent selected from the group consisting of an alkyl group, a cycloalkyl group, an alkenyl group, an alkynyl group, an aryl group, an arylalkyl group, an aromatic heterocycle, a heterocycle group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, an ureido group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group and a silyl group.

6. The photoelectric conversion element of claim 3, wherein the transparent electroconductive material comprises an indium-tin oxide.

7. The photoelectric conversion element of claim 1, wherein the substituent other than hydrogen is an aryl group, an arylalkyl group, or an aromatic heterocycle.

8. The photoelectric conversion element of claim 7, wherein the substituent other than hydrogen is a phenyl group, a naphthyl group, a biphenyl group, a methylaryl group, an ethylaryl group, an isopropylaryl group, an n-butylaryl group, a p-tolyl group, a p-ethylphenyl group, a p-isopropylphenyl group, a 4-propylphenyl group, a 4-butylphenyl group, or a 4-nonylphenyl group.

9. The photoelectric conversion element of claim 7, wherein the substituent other than hydrogen is a pyridyl group, a thienyl group, a furyl group, a pyridazinyl group, a pyrimidinyl group, a pyrazinyl group, a triazinyl group, an imidazolyl group, a pyrazolyl group, a thiazolyl group, a quinazolinyl group, or a phthalazinyl group.

10. The photoelectric conversion element of claim 1, wherein the substituent other than hydrogen is an alkyl group, an alkenyl group, or an alkynyl group.

11. The photoelectric conversion element of claim 10, wherein the substituent other than hydrogen is a methyl group, an ethyl group, a propyl group, an isopropyl group, a tert-butyl group, a pentyl group, a hexyl group, an octyl group, a dodecyl group, a vinyl group, or an ethynyl group.

12. The photoelectric conversion element of claim 1, wherein the substituent other than hydrogen is a cycloalkyl group or a heterocycle.

13. The photoelectric conversion element of claim 12, wherein the substituent other than hydrogen is a cyclopentyl group, a cyclohexyl group, a pyrrolidyl group, an imidazolidyl group, a morpholyl group, or an oxazolidyl group.

14. The photoelectric conversion element of claim 1, wherein the substituent other than hydrogen is an alkoxy group, a cycloalkoxy group, or an aryloxy group.

15. The photoelectric conversion element of claim 14, wherein the substituent other than hydrogen is a methoxy group, an ethoxy group, a propyloxy group, a pentyloxy group, a hexyloxy group, a cyclopentyloxy group, a cyclohexyloxy group, a phenoxy group, or a naphthyloxy group.

16. The photoelectric conversion element of claim 1, wherein the substituent other than hydrogen is an acyl group, an acyloxy group, an alkoxycarbonyl group, an aryloxycarbonyl group, or a thiocarbonyl group.

17. The photoelectric conversion element of claim 16, wherein the substituent other than hydrogen is an acetyl group, an ethylcarbonyl group, a propylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, a pyridylcarbonyl group, an acetyloxy group, an ethylcarbonyloxy group, an octylcarbonyloxy group, a phenylcarbonyloxy group, a methyloxycarbonyl group, an ethyloxycarbonyl group, a butyloxycarbonyl group, an octyloxycarbonyl group, a phenyloxycarbonyl group, a naphthyloxycarbonyl group, a thioacetyl group, an ethylthiocarbonyl group, a propylthiocarbonyl group, a cyclohexylthiocarbonyl group, an octylthiocarbonyl group, a 2-ethylhexylthiocarbonyl group, a dodecylthiocarbonyl group, a phenylthiocarbonyl group, a naphthylthiocarbonyl group, a pyridylthiocarbonyl group, 18. The photoelectric conversion element of claim 1, wherein the dioxaanthanthrene-based compound is selected from the group consisting of:

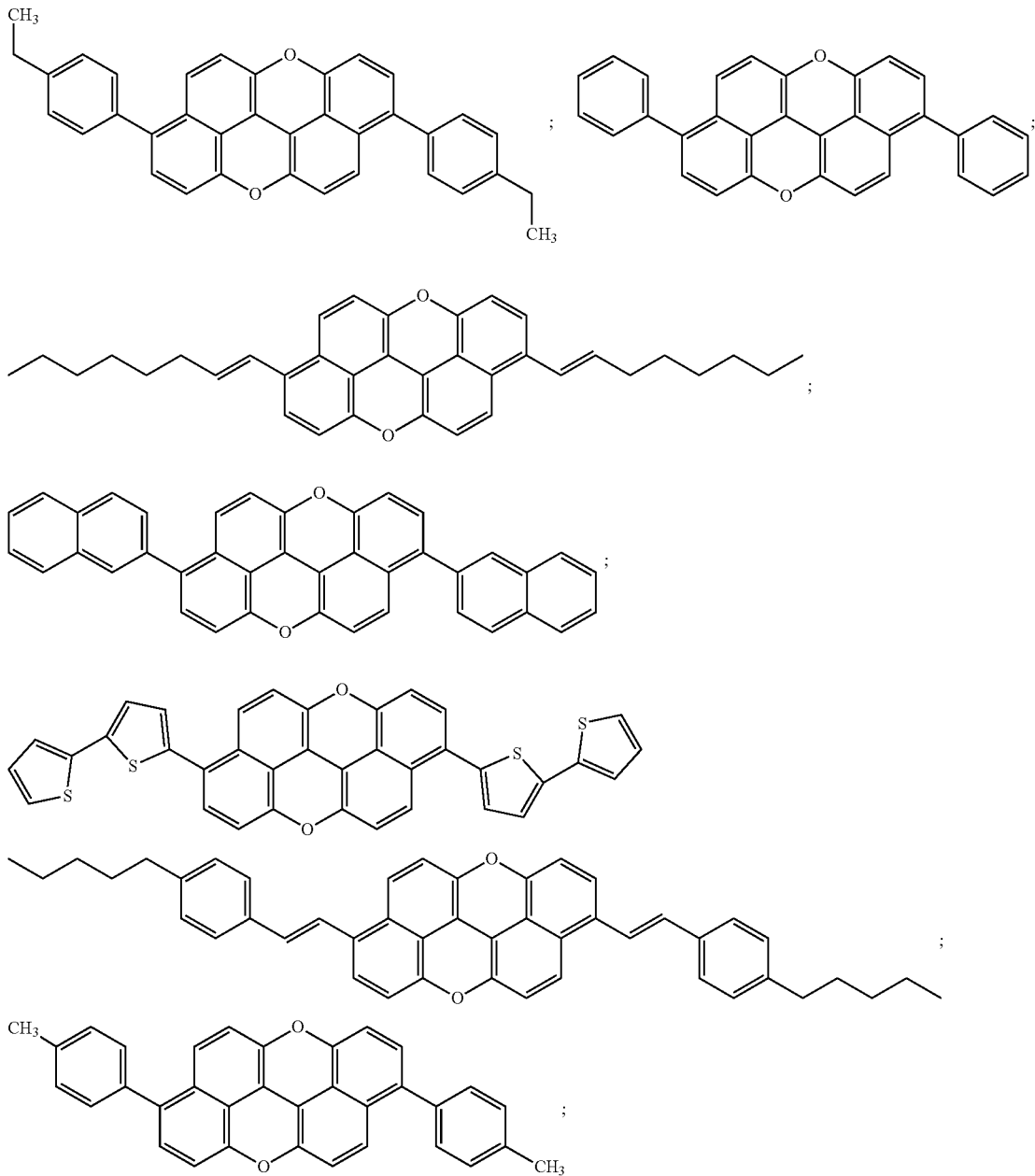

-continued
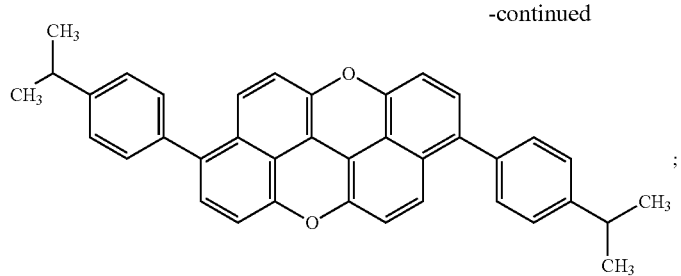
;
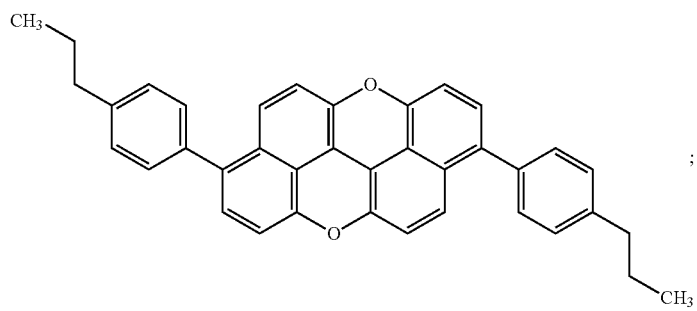
;
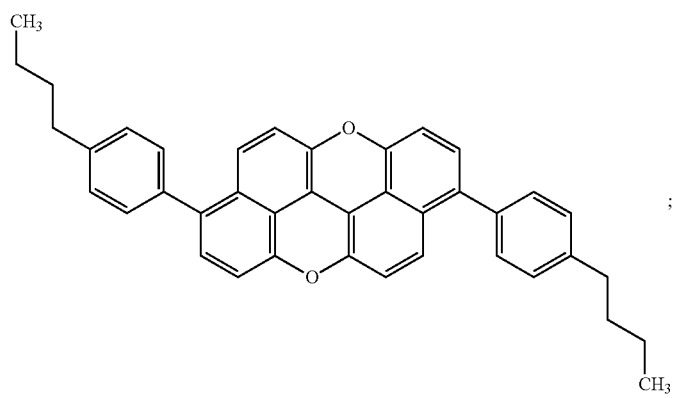
;
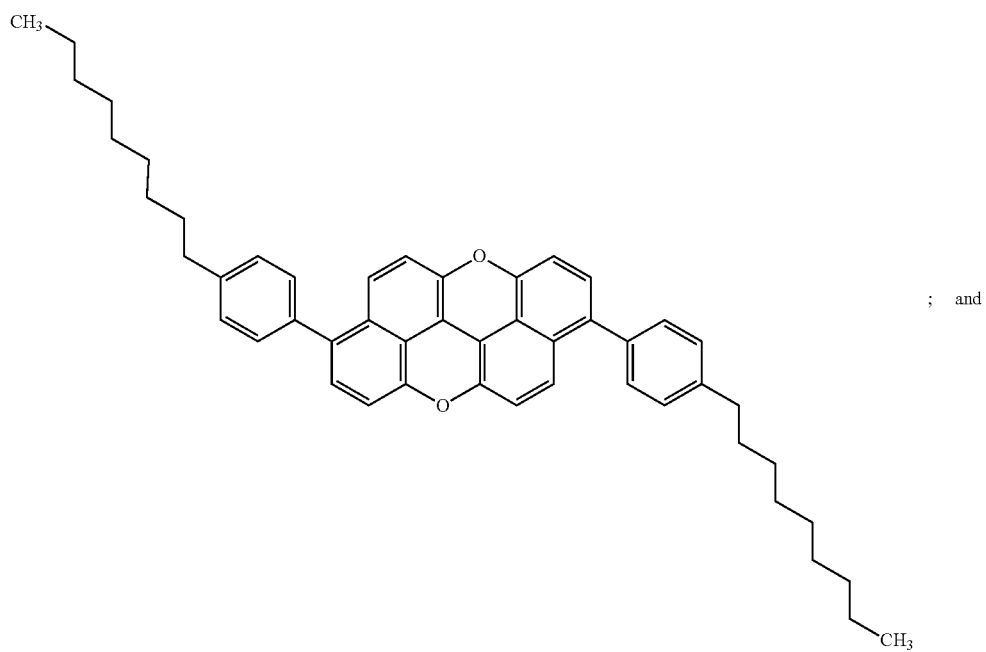
; and

-continued
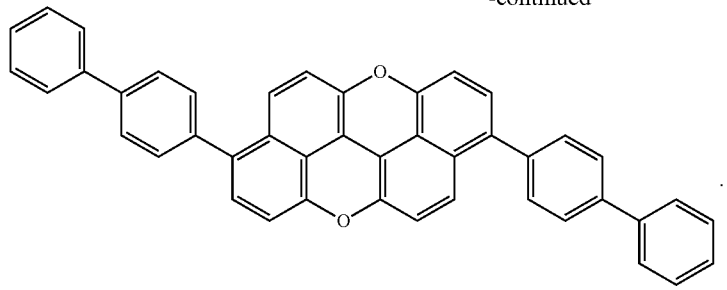
* * * * *